United States Patent [19]

Woon et al.

[11] 4,050,462
[45] Sept. 27, 1977

[54] DISPOSABLE DIAPER WITH ELASTICALLY CONSTRICTED CROTCH SECTION

[75] Inventors: Lin-Sun Woon; Dan D. Endres, both of Appleton, Wis.

[73] Assignee: Kimberly-Clark Corporation, Neenah, Wis.

[21] Appl. No.: 671,177

[22] Filed: Mar. 29, 1976

[51] Int. Cl.² .......................................... A61F 13/16
[52] U.S. Cl. .............................. 128/287; 128/290 R
[58] Field of Search .................... 128/284, 287, 290 R

[56] References Cited

U.S. PATENT DOCUMENTS

| | | | |
|---|---|---|---|
| 2,538,758 | 1/1951 | Bricmont | 128/287 |
| 2,627,859 | 2/1953 | Hargrave | 128/287 |
| 3,000,381 | 9/1961 | Mulhole et al. | 128/284 |
| 3,407,813 | 10/1968 | Grippo et al. | 128/287 |
| 3,417,751 | 12/1968 | Murdoch | 128/287 |
| 3,461,872 | 8/1969 | McConnell et al. | 128/287 |
| 3,658,064 | 4/1972 | Pociluyko | 128/287 |
| 3,776,233 | 12/1973 | Schaar | 128/287 |
| 3,860,003 | 1/1975 | Buell | 128/287 |

Primary Examiner—Aldrich F. Medbery
Attorney, Agent, or Firm—Daniel J. Hanlon, Jr.; William D. Herrick; Raymond J. Miller

[57] ABSTRACT

A disposable, single-use, generally elongate diaper having substantially planar sections at each end and intermediate these planar ends a substantially non-planar section comprising the crotch section. The crotch section is narrower than at least one of the ends and is longitudinally constricted by elastically extendible means secured to each of the edges of the crotch section in a manner which produces a plurality of gross transverse rugosities across the width of the crotch section of the diaper when the elastic means is in non-extended condition. The width dimension of the crotch is preferably within a predetermined percentage range of the combined width of the planar waist sections. The length dimension of the narrower crotch section is preferably a specified percentage of the full unconstricted length of the diaper. A further improvement is obtained if the geometry of the side edges between the wide waist section and the narrower crotch section is defined by a concave arc.

14 Claims, 9 Drawing Figures

DISPOSABLE DIAPER WITH ELASTICALLY CONSTRICTED CROTCH SECTION

BACKGROUND OF THE INVENTION AND REVIEW OF THE PRIOR ART

Disposable diapers are generally well known in the art and are becoming increasingly acceptable in the marketplace as a sanitary protection item, especially for use in infant and child care to absorb urine and fecal discharges. Unitary, preshaped or prefolded diapers which are generally comprised of a porous facing layer, a fluid impervious backing sheet and a highly absorbent batt sandwiched therebetween, which require no supplementary holders or panties, and which may be disposed of after a single use, have proved to be especially popular. Even though such diapers are growing in popularity, one feature which still appears to need improvement is obtaining a better, more satisfactory, fit. In discussing the problem of fit with mothers it was found that, while they wanted a diaper which neatly conformed to the child with a minimum of bulk and a maximum of comfort, what would really be more desirable to them than an aesthetically neat fit would be a diaper which minimized leakage both at the waist and at the crotch or thigh area.

Commercially successful attempts to improve fit in the past have involved geometrical folding of rectangular diapers for the purpose of narrowing the apparent width in the crotch area to facilitate application to the child. Typical examples of two variations of such prior art folds may be found in U.S. Pat. No. Re 26,151 to Duncan et al in which a rectangular diaper is provided with parallel longitudinal folded box pleats and a loose overlying flap along each side, and in U.S. Pat. No. 3,196,874 to Hrubecky in which a rectangular diaper is provided with triangular-shaped infolds in the crotch area. While these prefolded constructions permit the diaper to be more easily applied to the child, some disadvantages remain with respect to eliminating or minimizing leaks during use. First, when these prefolded rectangular diapers are used there is excess bulk between the legs which may cause discomfort; second, the folds of these rectangular diapers are generally linear and the relatively non-conformable structure of disposable diapers prevents a closely conforming fit at the buttocks or thighs, often leaving undesirable gaps in those two areas which permit leaks to occur; and third, when applied to the child the non-conforming sides of the rectangular diaper tends to pull the waist down at the sides and thereby cause the diaper to gap at the front of the waist where leaks can then occur.

Attempts to reduce bulk between the legs such as by reducing the width of the absorbent pad in the crotch area have also been tried, but again, because the materials used in constructing disposable diapers are relatively non-conformable, a close fit at the thigh is difficult to achieve and undesirable gaps still occur. In addition, the reduced width of the absorbent pad component cuts down on the available absorbent capacity in the crotch area which is another cause of leakage because of an inability of the reduced amount of material to adequately absorb urine in an area of the diaper where good absorbent capacity is most needed. One suggestion for eliminating such gaps at the narrowed crotch area was to provide the diaper edges with elasticized thin flexible flaps at least three-fourth inch in width when measured from the elasticized line to the edge of the absorbent pad in the crotch area as described in U.S. Pat. No. 3,860,003 to Buell. While this modification apparently provides a seal at the thighs because the tensioned elastic presses the easily deformable flap into close contact with the legs, mothers who tested diapers made in accordance with the structure described in the patent expressed several objections. First, they found that discharged fluids collected near the diaper edges and sometimes permeated into the interface between the flap and the skin where it could cause skin irritation aggravated by the tight fit of the elastic holding the flap against the skin; second, because it was necessary to reduce the width of the pad in the crotch area in order to provide the required flap width, the smaller amount of absorbent material available appeared to become excessively wet in use and, even though the elastic present in the flaps seemed to provide a tight seal at the leg, some leaks still occurred; and third, when the reduced width pad did become excessively wetted it tended to bunch up or disintegrate and hinder fluid transfer to other unused parts of the pad.

An older U.S. Pat. No. 2,273,542 to Tasker relating to disposable diapers suggests that a rectangular diaper can be made to fit better around the legs by elasticizing the entire length of the side edges so they are stretchable in an endwise direction. In this structure, the elastic provides transverse wrinkles in the full width of the diaper and when such a diaper is applied to a child it is stated that these wrinkles will open to form a sack in the crotch area. While this may be true, the full rectangular configuration of the diaper still leaves excessive bulk and width between the thighs, and leg action then tends to pull the diaper down and cause gaps at the waist. The full length elastic also makes fastening at the sides of the waist less convenient.

This invention is directed to an improved disposable diaper, in which the absorbent batt in the crotch area is of decreased width as compared to the waist to provide less bulk in the transverse direction. The diaper is elasticized only along the edges in the narrowed crotch area in a manner to give a more conformable leg fit as well as improved functional absorbent capacity. Attaching the elastic immediately adjacent to the batt edges and also bonding the batt surface to the backing or facing in that area to unitize the structure forces the batt to contract as the elastic contracts thereby longitudinally condensing the batt and producing gross transverse rugosities in the crotch area whereby an increase in the effective absorbent capacity of the batt in that area is also obtained. Limiting the elasticized edges to the narrowed crotch area foreshortens and provides transverse rugosities in the diaper batt only in the crotch area while minimizing the development of gaps at the waist.

SUMMARY OF THE INVENTION

Disposable diapers made in accordance with this invention are of the single-use type generally comprised of a porous facing sheet, a fluid impervious backing sheet and a highly absorbent batt sandwiched between such sheets and bonded to at least one of the sheets.

The diaper is generally elongate with substantially planar sections at each end which comprise the waist-encircling means when applied to a child, and a substantially narrower non-planar crotch section disposed between and joined to said planar waistband sections. The narrower crotch section is longitudinally constricted by an elastically extendible means secured to the backing sheet or the facing sheet adjacent each of the side edges of the narrower crotch portion. The elements of the diaper are bonded to each other at least in the crotch area so that when the elastic is constricted, or in nonextended condition a plurality of gross transverse rugosities are provided across the width of the crotch section.

The width dimension of the narrower crotch section is within a predetermined percentage range of the width dimension of the waist section, i.e., within the range of about 30% to 46% of the effective circumference of the waist sections as subsequently defined herein, with 35% to 40% preferred.

The length dimension of the narrower crotch section in its fully extended condition is also preferably a specified percentage of the fully extended length of the diaper, i.e., within the range of about 30% to 75%, with 60% preferred.

A further improvement in fit of the diaper of this invention is also obtained if the geometry of the side edges in the transition from the wider waist section to the narrower crotch section comprises a concave arc. A suitable geometry for the transitional arc located at the back portion of the diaper where the fastening tapes are normally pre-attached may be defined as a section of circle with a radius of between 20 and 22% of the gross circumference of the waist sections, a subsequently defined herein. The length of the arc may be defined by an enclosed angle which is preferably about 45° to 50°. A suitable geometry for the transitional arc located at the opposite front portion of the diaper may be defined as a section of a circle with a radius of 9 to 11% of the gross circumference of the waist sections, with an enclosed angle of about 65° to 75°.

Other features, objects, and advantages of the invention will become apparent by reference to the following detailed description and accompanying drawings.

DETAILED DESCRIPTION OF THE DRAWINGS AND PREFERRED EMBODIMENTS

Figure 1:
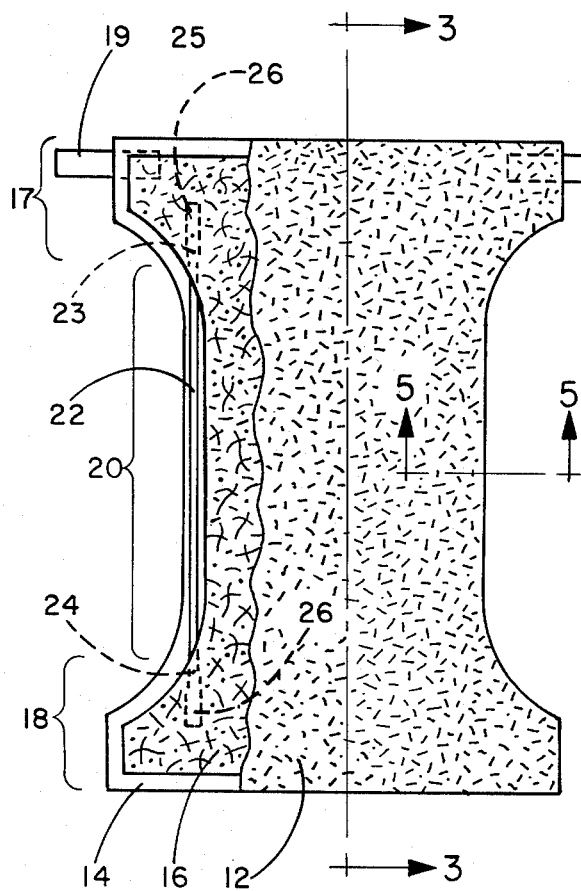
FIG. 1 is a plan view of a preferred embodiment of a disposable diaper of this invention with a portion cut away showing construction details and with the elastically extendible member in fully extended condition.
Figure 2:
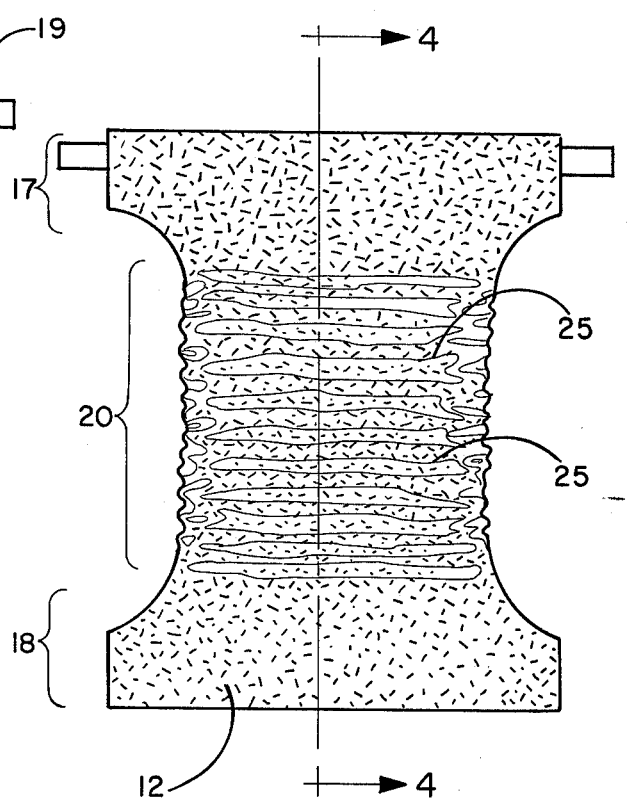
FIG. 2 is a plan view of the diaper of FIG. 1 but with the elastically extendible member in relaxed or unextended condition.
Figure 3:
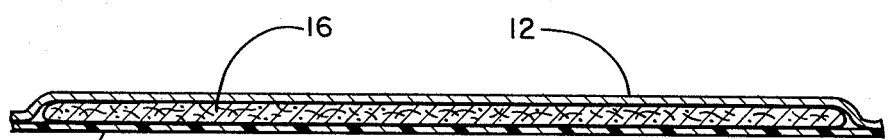
FIG. 3 is a section taken along lines 3—3 of FIG. 1.
Figure 5:
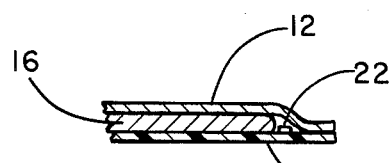
FIG. 5 is a partial sectional taken along lines 5—5 of FIG. 1.

As shown in the plan view of FIG. 1 and sectional views of FIGS. 2 and 5, a preferred embodiment of the diaper is of an elongate generally I shape, with a fluid permeable facing sheet 12, a fluid impervious backing sheet 14, and a highly absorbent batt 16 sandwiched between the facing and backing sheets.

The diaper is divided into waistband sections 17 and 18 at each end and a central narrowed-down crotch section 20 disposed between the waistband sections. During use, waistband section 17 is disposed at the back of the infant and may from time to time be referred to herein as the back portion of the diaper, while section 18 is disposed at the front and may from time to time be referred to herein as the front portion of the diaper. Conventional pressure sensitive tapes 19 are attached to the backing near the edges of section 17 for fastening purposes, although other suitable fastening means may be used. Such tapes are usually attached near the back portion of the diaper. One surface of absorbent batt 16 is bonded to backing sheet 14 or facing sheet 12 in at least the crotch section 20. Preferably, the absorbent batt is bonded to backing sheet 14 in the crotch section. Such bonding may be done by the use of strips of double-faced pressure sensitive tape, by trips of hot melt or pressure sensitive adhesive, by overall or patterned heat sealing, by a printed pattern of adhesives, or the like. Generally, attachment should be such that when the sheet to which the batt is bonded is constricted in its longitudinal direction by elastic means 22 disposed near the batt edges, the batt will also be constricted and convoluted thereby.

Figure 4:
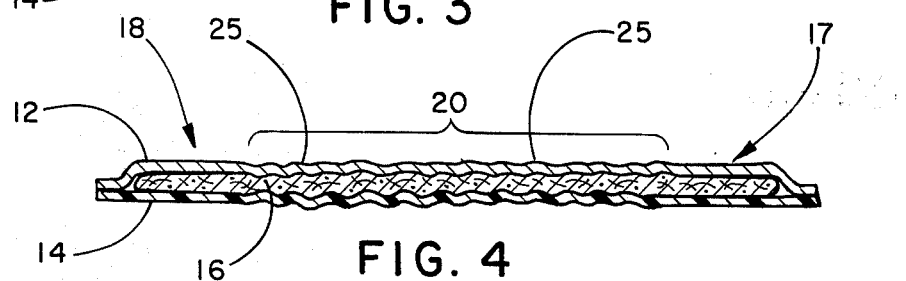
FIG. 4 is a section taken along lines 4—4 of FIG. 2.

Each edge of the diaper in the narrow crotch section 20 is provided with an elongate elastic means 22 secured in extended condition to backing sheet 14 or facing sheet 12 along the entire length of crotch section 20. In FIG. 1 this length lies between points 23 and 24. The free ends 26 of the elastic means positioned beyond these points are not fastened to either sheet and in the finished form of the diaper are not under tension, performing no function in the finished structure. The elastic means is fully stretched and under tension only during the manufacturing process when it exists as a continuous length for convenience in the process. The diaper is in its fully extended condition as shown in FIG. 1 only during the manufacturing process when a series of diapers are attached to each other in the form of a continuous strip. When this continuous strip is cut into individual diapers the elastic means is also cut and when thus relieved of its tension contracts from its fully extended condition, causing the crotch section of the diapers to contract in the elasticized area as shown in FIGS. 2 and 4. As indicated therein, waistband sections 17 and 18 are not constricted and remain substantially flat or planar because of the absence of a tensioned elastic member in those sections. When narrow crotch section 20 is constricted by the contracted elastic means at each edge, the crotch section develops a multiplicity of gross transverse rugosities 25. Stated another way, crotch section 20 is reduced in length but still contains the same amount of absorbent material. Accordingly, the absorbent batt in the crotch area is made effectively thicker because of the adjoining hills and valleys of which the transverse rugosities are comprised and therefore will have more absorbent capacity per unit area than a batt of the same original thickness has in its initial planar form.

In addition to making the diaper effectively more absorbent in the crotch area, the cushioning effect of the pad element forming these rugosities serves to relieve some of the pressure of the tensioned elastic means 22 where it presses the diaper into contact with the infant's skin when the diaper is worn. Accordingly, even though the elastic means will be under tension due to its being partially stretched out when the diaper is applied to the child, the transverse rugosities remaining in the absorbent pad act as cushions and tend to reduce the possibility of the elastic indenting or marking the skin. Such indentation or marking is more likely to happen when the tensioned elastic means is part of a thin flexible flap as in the prior art, thus permitting more intimate contact with the skin.

Figure 6:
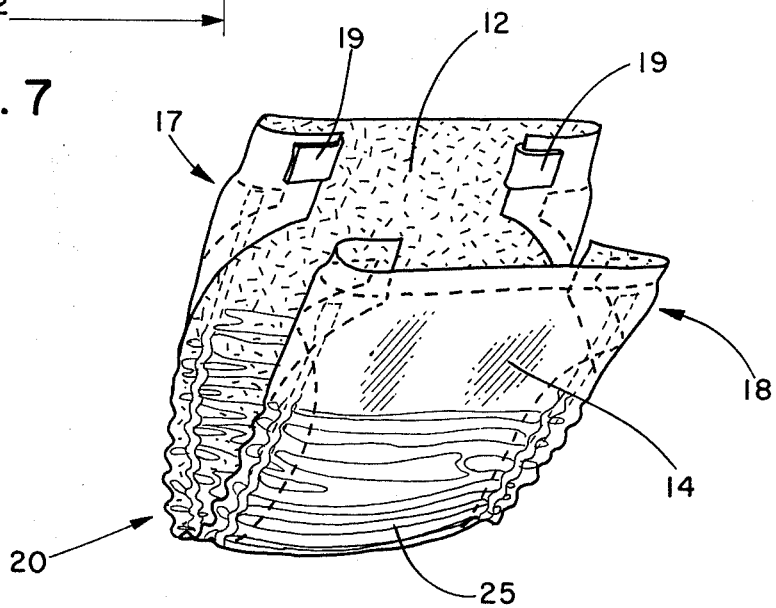
FIG. 6 is a perspective view of the diaper of FIG. 2 in a folded condition ready for packaging.

The FIG. 6 illustration is presented primarily to show how conveniently the diaper of this invention may be folded and adapted for packaging. The foreshortening of the narrow crotch section by the elastic tends to cause the diaper to fold itself transversely in half with the facing sheet inward. The outwardly extending ears at the edges of the waistband sections are then easily folded inward, and since the rugose crotch section is effectively thicker than the planar waistband sections, the inwardly-folded waistband sections are easily accommodated by the less thick planar areas to provide a neatly folded diaper for packaging which in its folded configuration is of substantially uniform thickness.

Figure 7:
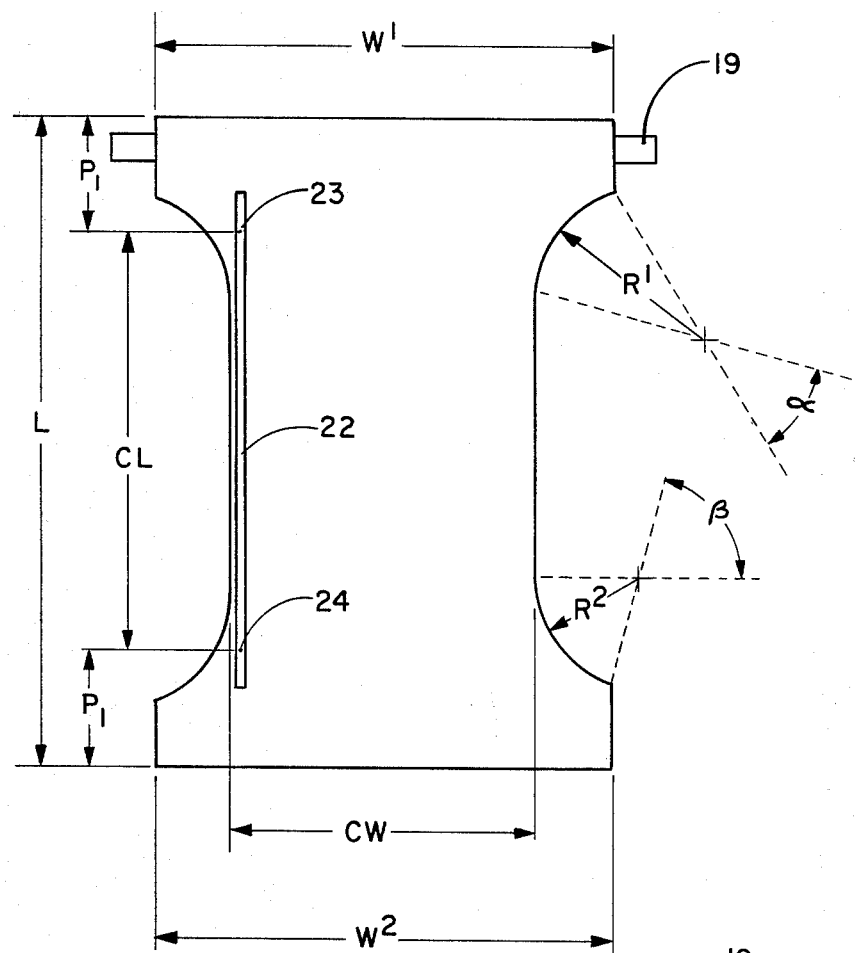
FIG. 7 schematically illustrates in plan view some of the preferred dimension relationships in an I-shaped diaper made in accordance with the invention.

In the schematic view of FIG. 7, some of the dimensions for the preferred diaper construction are shown. As indicated in this figure, $W^1$ and $W^2$ indicate the width dimensions for the back and front waistband sections, and as shown in this embodiment these dimensions are the same and wider than the intermediate crotch area. L represents the overall extended length of the diaper. CL represents the length of the crotch section as well as the effective length of the elasticized area between points 23 and 24. $P^1$ and $P^2$ indicate the longitudinal dimension of the back and front planar waist sections respectively. $R^1$ and $R^2$ indicate the radii of the circular concave arcs which respectively define the back and front transitional curves of the diaper edges from the straight edges of the wide waist section and edges of the narrow crotch section. Angle $\alpha$ defines the length of the circular arc of the transitional curve at the back portion of the diaper and angle $\beta$ defines the length of the circular arc of the transitional curve at the front portion of the diaper.

In the development of the diaper of this invention it was found that the width of the crotch section and particularly the absorbent batt in that section has an important effect on the ability of the diaper to fit reasonably well while minimizing leg leakage, i.e. leakage at the thigh. It was also found that this preferred range of crotch width has a definable relationship with respect to the dimension of effective waist circumference measurement of the diaper. Stated another way, there is an optimum range for the crotch width for each waist dimension.

In general, disposable diapers have been grouped into three standard sizes by the manufacturers. A Newborn size diaper is in the vicinity of 14 inches long and 10 inches wide in overall dimensions. A Medium size diaper is about 16 inches long and 11¼ inches wide, and a Toddler and/or Overnite size diaper is about 17½ inches long and 13 inches wide. When applying diapers to an infant the mother usually provides about 2 inches overlap at each side, accordingly the effective waist circumference measurement, hereinafter designated EWCM, is considered to be the sum of the width of the waistband sections minus 4 inches.

In the FIG. 7 drawing then, the EWCM for any particular size diaper may be defined as $W^1 + W^2 - 4$ inches. Accordingly for a Toddler size diaper in which $W^1$ and $W^2$ are 13 inches, EWCM = 22 inches. For the Medium size diaper where $W^1$ and $W^2$ are 11½ inches, EWCM is 19 inches and for Newborn size diapers where $W^1$ and $W^2$ are 10 inches, EWCM is 16 inches.

For purposes of this invention, the most effective crotch width dimension for any particular diaper size lies between about 30% and 46% of the EWCM, with about 35% to 40% preferred.

Figures 8, 9:
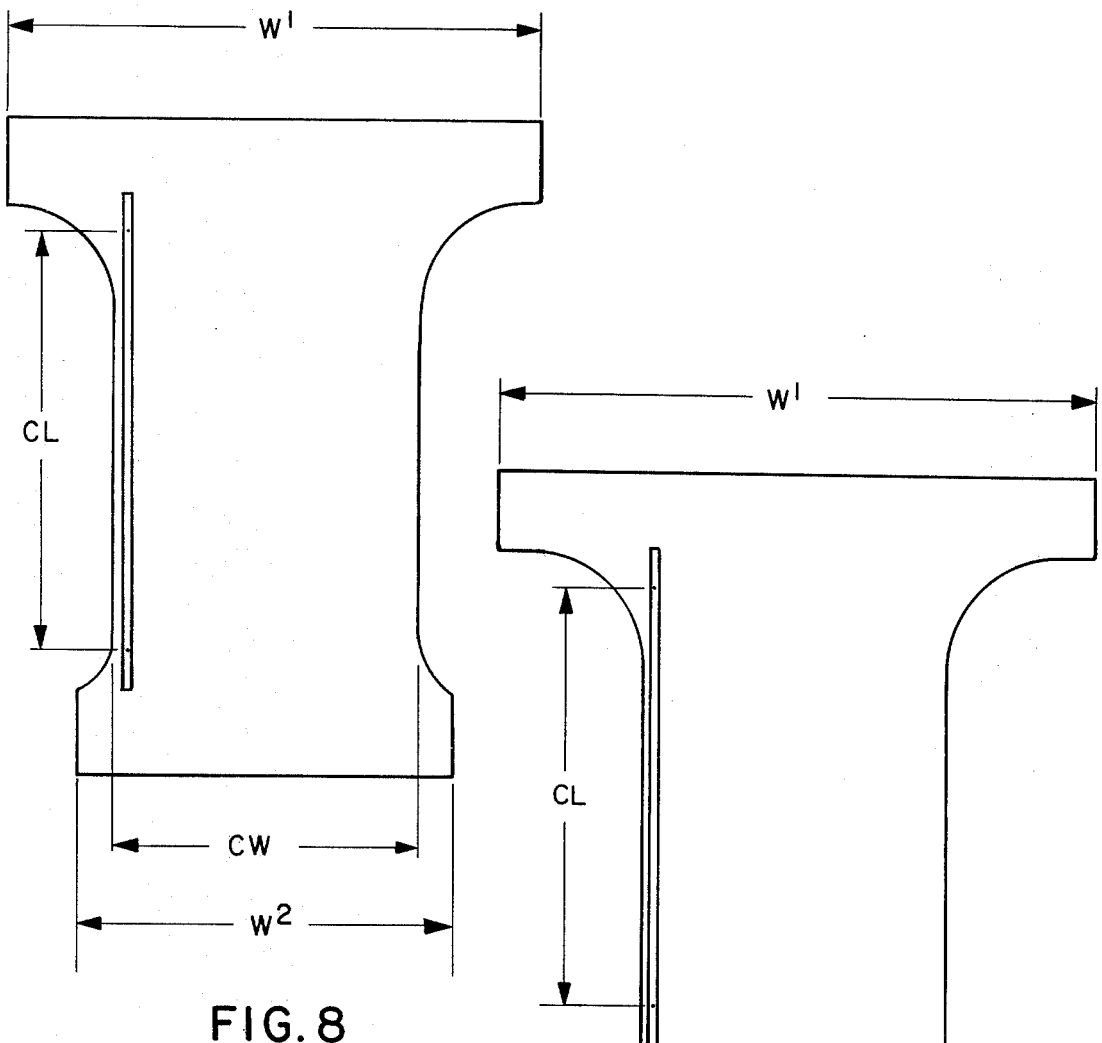
FIGS. 8 and 9 schematically illustrate in plan view dimensional relationships for other less preferred embodiments.

While the preferred shape of diapers made in accordance with this invention is the I configuration shown in FIGS. 1 to 7, the concept is adapted to other modified shapes such as shown in FIGS. 8 and 9. The prime consideration is that the width in the narrow crotch portion be within a specified percentage range of the effective waist circumference measurement. Thus, whether or not one waistband section is wider than the other is not critical, it is the addition of the $W^1$ and $W^2$ dimensions which determines the relationship of waist measurements to crotch dimension.

While other shapes such as shown in FIGS. 8 and 9 are less desirable the advantages of the invention described herein are applicable thereto.

The length of the elasticized area in the diaper of this invention also has preferred dimensional relationship to the overall length of the diaper. This elasticized length is indicated by the dimension CL in FIG. 7. The effective range for elasticized length dimension is from 30% to 75% of the overall length (L in FIG. 7) of the diaper with 60% preferred. The length of planar areas $P^1$ and $P^2$ in FIG. 7, therefore will each be about one-half of the remaining percentage, although the exact length may vary somewhat.

In defining the geometry of the concave arcuate transition areas between the end waistband sections of the diaper and the narrow central crotch section, the dimensions defined below have been found to provide diapers which fit smoothly and snugly across buttocks and in the frontal thigh and abdominal regions. For the back portion of the diaper where the fastening tapes 19 are normally attached, the transitional concave arc from the waistband side edge to the crotch section edge is preferably the arc of a circle with a radius ($R^1$) of 18 to 30% of the gross circumference of the diaper with 20 to 22% preferred. The length of this arc as defined by the enclosed angle $\alpha$ should not be less than 30° and preferably is between 45° and 50°. For the front portion of the diaper the radius of the circular arc is normally about one-half of the radius of the back curve or about 9 to 15% of the gross circumference of the diaper and preferably is 9 to 11%. The enclosed angle $\beta$ of the front arc should not exceed 90° and preferably is between 65° to 75°. For purposes of this invention, the gross circumference of the diaper is equal to the sum of the width of the waistband sections, or $W^1 + W^2$. While circular arcs are preferred as the best geometric form defining the transition areas there are other curves; for example, the ellipse, the hyperbola and various exponential curves; which, by proper selection can closely approximate the shape of a circular arc. The most critical zone of the transition curve is the middle half of the respective enclosing angle, and it is preferred that at least this portion be circular.

A suitable material for the absorbent batt used in the diaper is an air-formed batt of wood pulp fibers commonly known as fluff. In one preferred example, the fluff batt weighed about 0.286 grams/sq. in. of area in its unconstricted condition as well as in the planar sections of the batt when the other portions of the diaper are constricted, and about 0.32 grams/sq. in. in the constricted crotch section of the batt. It is preferred that effective weight of the absorbent material in the constricted crotch area be at least 15% greater per unit area than the weight of the absorbent material in the planar area. The thickness of the same fluff batt in unconstricted condition was measured at about 0.755 inches and in constricted condition about 1.27 inches. The constricted batt therefore had more effective thickness in the constricted area. Depending on the size diaper being selected, the starting flat or planar weight and thickness may be suitably varied, i.e. thinner for the smaller sizes, thicker for the larger sizes.

As indicated earlier, in order for the elastic means to be capable of constricting the batt to produce the desired transverse rugosities, the batt should be bonded to either the backing sheet or the facing sheet in at least the crotch section. This bonding preferably is to the backing sheet, particularly when the elastic is also bonded to the backing sheet. In addition, the elastic means should be disposed as close to the edge of the batt in the crotch section as is physically possible and still consistent with good manufacturing practices. If the elastic means is located too far from the edge it will not constrict the fluff batt sufficiently to produce the desired transverse rugosities because the backing sheets or facing sheets are too flexible and will absorb all the constricting force while transmitting substantially none to the batt. In such cases, when this thin flexible member is constricted without being restrained by the batt it produces a fine-grained, crepe-like structure in the flap only rather than the desired gross rugosities in the batt. With such a thin flexible edge, the tension of the elastic will hold the thin flap, which results in the absence of a restrictive batt, tightly against the skin, and because the backing is of substantially non-breathable material will tend to maintain a damp condition at the interface of flap and skin causing undesirable skin hydration.

It is preferred that the elastic member be contiguous to the edge of the batt in the narrow crotch section, and that the elastic be spaced no farther than 1/2 inch from the batt edge. Generally speaking, the elastic should be sufficiently close to the batt edge to assure that the desired transverse rugosities are developed in the absorbent batt when the elastic is constricted. The elastic means may comprise rubber or any material with rubberlike properties that is capable of retracting after being stretched. It may be used in the form of flat strips, multiple strands, round or square filaments or any other available shape or make-up.

As indicated earlier the basic components which are combined to make up disposable diapers of this invention are generally conventional types, i.e., a fluid pervious facing sheet, a fluid impervious backing sheet and a highly absorbent batt disposed between the two sheets in unitary assembly. The specific components may be any of the common type used for such purposes. The fluid pervious facing sheet may be any soft, flexible porous sheet which permits the passage of fluids therethrough including hydrophobic or hydrophilic non-woven webs, wet strength papers, spunwoven filament sheets and the like. A particularly suitable sheet is one made of spunwoven polypropylene filaments with spot embossing, and preferably with a preforated surface or suitable surfactant treatment to aid fluid transfer. The backing sheet is preferably a thin plastic film such as polyethylene, polypropylene, polyvinylchloride or the like. It is preferably opaque with an embossed or matte surface. The absorbent batt preferably is an airformed pad of wood pulp fibers known in the art as fluff. Other absorbent materials, alone or in combination and including webs of carded or airlaid textile fibers, multiple plies of creped cellulose wadding, various super absorbent materials, synthetic foam sheets or the like may also be used. The batt may also be slightly compressed or embossed in selected areas as desired.

It is important that the absorbent batt should also be bonded to at least one of the outer sheets, preferably the backing sheet, in a manner such that when the elastic member contracts the sheet to which the elastic is attached, the batt will also be forced to contract.

One simple form of assembly is to have all three components of the same peripheral configuration with the borders of both the facing sheet and backing sheet extending slightly beyond the borders of the batt. As shown in FIG. 1, the facing sheet and backing sheet can then be bonded together around the entire periphery of the batt to provide a neat, sealed construction. Other means of assembly may be used, such as turning over the edges of the backing sheet on top of the facing sheet, or vice versa, and securing these turned-over edge portions in place.

Also as indicated earlier, it has been found that when the batt is in its transversely rugose or corrugated form it appears to have more wet stability. That is, when the batt is saturated with urine and severely flexed by the normal body motions of an active child the batt does not ball up or disintegrate easily as a batt which is maintained in planar form. Because of this the batt is capable of more effectively using its available absorbent capacity as well as maintaining a neater overall appearance wet or dry.

What is claimed is:

1. In a disposable, unitary and generally elongate diaper having a substantially planar waist-band section at each end and a narrow substantially non-planar crotch section disposed between said ends in which said diaper is comprised of a porous facing sheet, a fluid-impervious backing sheet and an absorbent batt disposed between said sheets and in which the peripheries of said facing and backing sheets adjacent said batt are joined to each other, the improvement wherein said narrow crotch section is longitudinally contracted over its entire width by elastically extendible means, said contraction being obtained by having at least one each of said elastically extendible means secured while in extended condition to at least one of said facing sheet or said backing sheet along the entire length of and adjacent each edge of said crotch section whereby when said elastically extendible means are relaxed and unextended the bonded together diaper structure across the entire width of the crotch section is contracted by said means into a plurality of gross transverse rugosities adjoining each other along the length of said crotch section.

2. The diaper of claim 1 wherein said elastically extendible means is a flat strip of elastic.

3. The diaper of claim 1 wherein the width dimension of said crotch section is within the range of about 30% to 46% of the effective circumference of the waist sections.

4. The diaper of claim 1 wherein the width dimension of said crotch section is within the range of about 35% to 40% of the effective circumference of the waist sections.

5. The diaper of claim 1 wherein the length dimension of the narrow crotch section is within the range of about 30% to 75% of the overall diaper length.

6. The diaper of claim 1 wherein the length dimension of the narrow crotch section is about 60% of the overall diaper length.

7. The diaper of claim 1 wherein the edges of the waist-band sections are substantially straight and parallel and the edges of the narrow crotch section are substantially straight and parallel and are joined to each other by a concave arc.

8. The diaper of claim 7 wherein said concave arc is a section of a circle.

9. The diaper of claim 7 wherein the concave arc at the back portion of the diaper is the arc of a circle with a radius of 18% to 30% of the gross circumference of the diaper.

10. The diaper of claim 9 wherein the length of said concave arc is defined by an enclosed angle of from about 30° to about 50°.

11. The diaper of claim 7 wherein the concave arc at the front portion of the diaper is the arc of a circle with a radius of 9% to 15% of the gross circumference of the diaper.

12. The diaper of claim 11 wherein the length of said concave arc is defined by an enclosed angle of from about 65° to 90°.

13. In a disposable unitary and generally elongate diaper having a substantially planar waist-band at each end and a narrower crotch section disposed between said ends, in which said diaper is comprised of a porous facing sheet, a fluid-impervious backing sheet peripherally joined to said facing sheet, and an absorbent batt of substantially uniform thickness disposed between said sheets with said batt being bonded to one of said sheets at least in the crotch section, the improvement wherein the entire width of said narrower crotch section is longitudinally constricted by elastically extendible means which means has been secured for its entire length while in extended condition to at least one of said facing and backing sheets adjacent each edge of said crotch section, the constriction of the diaper structure in said crotch when said extendible means is contracted to unextended condition thereby providing the entire width of the crotch area with transverse rugosities comprised of hills and valleys to make the diaper effectively thicker in the crotch area and thereby providing the constricted crotch area with an effective weight of absorbent material per unit area when measured in constricted condition which is greater than the effective weight of the absorbent material per unit area when unrestricted as in the planar area.

14. The diaper of claim 12 in which the effective weight of the absorbent material in the constricted crotch area is at least 15% greater than the effective weight of the absorbent material in the planar area.

* * * * *